United States Patent [19]

Orr

[11] Patent Number: 4,560,507

[45] Date of Patent: Dec. 24, 1985

[54] PREPARATION OF 1-BENZYLAZETIDIN-3-OL

[75] Inventor: Alexander F. Orr, Kent, England

[73] Assignee: Shell Oil Company, Houston, Tex.

[21] Appl. No.: 604,696

[22] Filed: Apr. 27, 1984

[30] Foreign Application Priority Data

May 4, 1983 [GB] United Kingdom ............... 8312104

[51] Int. Cl.$^4$ .......................................... C07D 205/04
[52] U.S. Cl. ............................................. 260/239 A
[58] Field of Search .................................... 260/239 A

[56] References Cited

U.S. PATENT DOCUMENTS 3,649,618  3/1972  Horrom ........................ 260/239 A
4,341,887  7/1982  Buriks et al. ............ 260/239 AR X

FOREIGN PATENT DOCUMENTS 1014404  1/1958  Fed. Rep. of Germany ... 260/239 A
1111638  7/1961  Fed. Rep. of Germany ... 260/239 A

OTHER PUBLICATIONS

Chatterjee, et al., Chemical Communications, Chemical Society (London), 1968, p. 93.
Gaertner, Tetrahedron Letters, No. 39, 1966, pp. 4691–4694.
Gaertner, J. Org. Chem., vol. 32, 1967, pp. 2972–2976.
Gibbs et al., J. Am. Chem. Soc., 57 (1935), pp. 725–727.
Mannich, et al., Ber., 70, (1937), pp. 210–213.
Ross, et al., J. Org. Chem., 29, (1964), pp. 824–826.
Nakagawa, et al., Chem. Abstracts, vol. 88, (1978) Abst. #62304c and vol. 82 (1975) #125293x.

*Primary Examiner*—Donald G. Daus
*Assistant Examiner*—William A. Teoli, Jr.

[57] ABSTRACT

1-Benzylazetidin-3-ol, a precursor to 3-carboxyazetidine, is prepared by heating N-benzyl-3-amino-1-chloropropan-2-ol in an aqueous medium, optionally treating the resulting hydrochloride salt with an alkali metal base.

3 Claims, No Drawings

PREPARATION OF 1-BENZYLAZETIDIN-3-OL

BACKGROUND OF THE INVENTION

3-Carboxyazetidine is of interest for selectively sterilizing the male parts of plants: European patent application No. 29265. It can be prepared from 1-benzhydrylazetidine-3-ol, which is prepared by the reaction of epichlorohydrin with benzhydrylamine: A. G. Anderson, Jr. and R. Lok, Journal of Organic Chemistry, 1972, volume 37, pages 3953–5. However, the introduction of a benzhydryl group is very inconvenient for an economically practicable synthesis route, since the size of that group greatly increases the bulk of material to be processed, only to be removed once its protective function is no longer required. It would be economically very desirable to use a protective group less bulky than the benzhydryl group, for example, the benzyl group, but previous attempts to react epichlorohydrin with benzylamine have failed to produce any significant yield of the desired cyclized azetidine product.

DESCRIPTION OF THE INVENTION

It now has been found that 1-benzylazetidin-3-ol can be prepared as follows:

(a) reacting epichlorohydrin with benzylamine to form the addition product, N-benzyl-3-amino-1-chloropropan-2ol (I);

(b) cyclizing I by heating it in an aqueous medium, to form 1-benzylazetidin-3-ol hydrochloride (II);

(c) treating (II) with an alkali metal base.

In step (a), the reaction preferably is conducted by mixing the reactants in an organic solvent, for example, a hydrocarbon solvent such as cyclohexane. Suitable reaction temperatures are from 10° to 50° C. and suitable reaction times are from 12 to 36 hours. The addition product (I) may be recovered from the reaction mixture by conventional procedures and, if desired, may be purified, for example, by recrystallization, before step (b).

The cyclization of addition product (I) is carried out in an aqueous medium which may be water itself or a mixture of water and a liquid organic material. The organic material may be chosen from a wide range of organic compounds, for example, hydrocarbons, such as toluene, halo-hydrocarbons such as carbon tetrachloride, tetrachloroethane or bromobenzene, alcohols such as methanol, isopropanol or n-butanol, ketones such as methyl isobutyl ketone, cyclo-ethers such as dioxane, esters such as ethyl acetate or nitro-compounds such as nitrobenzene. The proportion of water in the mixture is suitably from 25 to 75% by volume. The cyclization preferably is carried out at elevated temperature, for example, from 50° to 150° C. Conveniently, the cyclization is carried out at the boiling point of the aqueous medium under reflux.

The immediate product of the cyclization step (b) is the hydrochloride salt of 1-benzylazetidin-3-ol. Treatment of this salt with an alkali metal base, such as the hydroxide, gives 1-benzylazetidin-3-ol, which may be recovered and purified by conventional procedures. A convenient procedure is to treat the aqueous solution of the hydrochloride salt obtained from step (b) with the base.

The invention is illustrated in the following examples. In each case, the identity of each product was confirmed by appropriate chemical and spectral analyses.

EXAMPLE 1

Preparation of 1-Benzylazetidin-3-ol (1)

(a) 46.25 g of epichlorohydrin, 33.5 g of benzylamine and 250 ml of cyclohexane were stirred together at ambient temperature for 24 hours. The precipitate formed was filtered off and recrystallized from toluene to give N-benzyl-3-amino-1-chloropropan-2-ol (1A), as a crystalline solid, m.p.: 70°–71° C., in 55% yield.

(b) 10 g of 1A was heated under reflux in 150 ml of water with stirring for 24 hours. The reaction mixture was cooled, the aqueous solution was decanted from insoluble material and made alkaline by the addition of solid sodium hydroxide. The oil which separated was extracted with dichloromethane and the extracts were washed with water and dried. The solvent was removed under reduced pressure and the residue was purified by chromatography on silica gel using acetone as eluent, followed by recrystallization from toluene to give 1, as a crystalline solid, m.p.: 64.5°–65.5° C., in 27% yield.

EXAMPLES 2 TO 12

The procedure of Example 1 was repeated, except that in step (b) the water was replaced by a 1:1 v:v mixture of water and an organic liquid. The results of these experiments are summarized in Table I.

TABLE I

| Example | Organic Liquid Component | Yield of 1-Benzylazetidin-3-ol % |
|---|---|---|
| 2 | toluene | 28 |
| 3 | tetrachloroethane | 27 |
| 4 | n-butanol | 26 |
| 5 | bromobenzene | 25 |
| 6 | methanol | 26 |
| 7 | nitrobenzene | 25 |
| 8 | isopropanol | 26 |
| 9 | methyl isobutyl ketone | 26 |
| 10 | dioxane | 27 |
| 11 | carbon tetrachloride | 27 |
| 12 | ethyl acetate | 25 |

Comparative Experiments

The procedure of Example 1 was repeated, except that in step (b) the water was replaced in turn by ethanediol, acetonitrile, methanol and butanol. In each case no 1-benzylazetidin-3-ol was formed.

EXAMPLE 13

Use of 1-Benzylazetidin-3-ol to Prepare 3-Carboxyazetidine (a) 5.0 g of 1-benzylazetidin-3-ol, 3.52 g of methane sulphonyl chloride, 6 ml of trimethylamine and 40 ml of dichloromethane were stirred together for 18 hours. The mixture was filtered and the solvent was removed under reduced pressure. The residue was purified by chromatography on silica gel using isopropanol in dichloromethane as eluent to give the mesylate of 1-benzylazetidin-3-ol (13A).

(b) 1.7 g of 13A and 1.2 g of sodium cyanide were stirred together in 1 ml of water and 20 ml of dimethylformamide at 60° C. for 16 hours. The solvent was removed under reduced pressure and the residue was purified by chromatography on silica gel using isopropanol in dichloromethane as eluent to give 1-benzyl-3-cyanoazetidine (13B).

(c) 1.5 g of 13B in 10 ml of saturated barium hydroxide solution was heated under reflux for 30 hours. The reaction mixture was cooled, saturated with gaseous carbon dioxide and filtered. The solvent was removed from the filtrate under reduced pressure to give 1-benzylazetidine-3-carboxylic acid (13C).

(d) 0.5 g of 13C in 15 ml of methanol was hydrogenated in the presence of a 5% palladium-on-carbon catalyst at room temperature. The catalyst was filtered off and the solvent removed from the filtrate under reduced pressure to give 3-carboxyazetidine.

I claim:

1. A process for preparing 1-benzylazetidin-3-ol, which comprises heating N-benzyl-3-amino-1-chloropropan-2-ol in an aqueous medium selected from water and mixtures of water and inert organic liquids.

2. A process for preparing 1-benzylazetidin-3-ol, which comprises heating N-benzyl-3-amino-1-chloropropan-2-ol in an aqueous medium selected from water and mixtures of water and inert organic liquids then treating the resulting product in an aqueous medium with an alkali metal base.

3. A process according to claim 2 in which the product is in solution in the original aqueous medium.

* * * * *